United States Patent [19]
Gainer

[11] Patent Number: 6,060,511
[45] Date of Patent: *May 9, 2000

[54] TRANS-SODIUM CROCETINATE, METHODS OF MAKING AND METHODS OF USE THEREOF

[76] Inventor: John L. Gainer, 125 Cameron La., Charlottesville, Va. 22903

[ * ] Notice: This patent issued on a continued prosecution application filed under 37 CFR 1.53(d), and is subject to the twenty year patent term provisions of 35 U.S.C. 154(a)(2).

[21] Appl. No.: 08/725,166

[22] Filed: Oct. 3, 1996

Related U.S. Application Data

[60] Provisional application No. 60/004,849, Oct. 5, 1995.

[51] Int. Cl.$^7$ ..................................... A61K 31/20
[52] U.S. Cl. .......................... 514/558; 514/557; 554/156; 554/202; 554/206; 554/223; 554/224
[58] Field of Search .................... 554/223, 224, 554/175, 206; 514/557, 558

[56] References Cited

U.S. PATENT DOCUMENTS 4,046,880  9/1977  Gainer ..................... 424/180
4,176,179 11/1979  Gainer ..................... 424/180

OTHER PUBLICATIONS

Streitwieser et al., Introduction to Organic Chemistry, 2nd ed., pp. 504–505, 1981.

*Primary Examiner*—Deborah D. Carr
*Attorney, Agent, or Firm*—Oblon, Spivak, McClelland, Maier & Neustadt, P.C.

[57] ABSTRACT

The use of crocetin has been demonstrated to be effective in elevating oxygen diffusivity, and increasing oxygen consumption by the body tissues of a mammal. Crocetin is difficult to solubilize. Sodium crocetinate, formed by reacting crocetin with sodium hydroxide, appears in several isomeric forms. The trans isomer is effective in improving oxygen diffusivity, while the related cis isomer appears not to be. Isolated TSC can be used in place of crocetin, treat a variety of conditions, including hypertension, cardiovascular disease, hemorrhagic shock, papillomas and related conditions.

6 Claims, 1 Drawing Sheet

TRANS-SODIUM CROCETINATE, METHODS OF MAKING AND METHODS OF USE THEREOF

This patent application claims priority of Provisional Patent Application 60/004,849 filed Oct. 5, 1995. Full benefit of priority from said parent provisional application is sought herein.

FIELD OF THE INVENTION

BACKGROUND OF THE INVENTION

This invention pertains to a compound which improves oxygen diffusivity from red blood cells to body tissues in mammals, including humans, methods of preparation, and methods of use thereof. Specifically, trans-sodium crocetinate (TSC herein) has been demonstrated to increase oxygen diffusivity, improve oxygen uptake, and is indicated for pharmaceutical utility in a wide variety of applications.

BACKGROUND OF THE PRIOR ART

Human metabolism requires that oxygen be supplied continuously to muscles, organs and various body tissues. Under normal conditions, sufficient oxygen is provided by the atmosphere to sustain life. The oxygen must be transferred to the body tissues in order to be used. The transfer pathway begins with transfer to the blood stream via the lungs, followed by transport as part of the Heme complex to various parts of the body, and finally, passing from the red blood cells to the various tissues. Thus, passage of the oxygen through the alveolar membranes of the lungs, the walls of the blood vessels, the blood plasma itself, red blood cell membranes and the interior of the tissues all provide barriers to oxygen transfer. The movement of oxygen across each barrier is "driven" by a concentration ingredient. If changes occur to that driving force, or to any of the resistances, the amount of oxygen reaching the tissue changes.

A wide variety of conditions, notably among them hemorrhagic shock, are controlled or be mediated by delivery of oxygen to body tissues. It has long been known that "oxygen delivery" to tissues is impacted by the oxygen concentration in the blood, as well as the rate at which blood is flowing. Repeatedly, however, there has been evidence suggesting that these two factors, generally referred to as "oxygen delivery" do not determine the total amount of oxygen consumed. Among other causative agents, the barriers described above pose potential problems. While the resistance of cell membranes to oxygen diffusion appears to be negligible, Wagner et al., J. Applied Physiol., 33:62–71 (1972) and Kreuzer et al., J. Applied Physiol., 15:1117–1122 (1960) there are indications that blood plasma offers a major barrier to oxygen consumption by the tissues. See, e.g., Huxley et al., J. Physiol., 316:75–83 (1981) and Holland et al., Resp. Physiol., 59:71–91 (1985). The inventor herein demonstrated that oxygen diffusivity can be improved, in mammalian models, by administration of the naturally-occurring carotenoid crocetin to the blood volume. Thus, improvements in oxygen diffusivity, oxygen consumption, and survival in rats with induced hemorrhagic shock was demonstrated by the inventor, Gainer et al., Circulatory Shock 41:1–7 (1993). An examination of oxygen uptake by stimulated muscles, and the effect of oxygen diffusivity and related parameters appears in Gainer, J. Applied Physiol. 76:1826–1829 (1994). The discovery that crocetin improves oxygen diffusivity, and the conditions treatable therewith, form the basis of a variety of patents related to the treatment of various conditions based on the use of crocetin. Included in this group are: U.S. Pat. Nos. 4,176,179; 4,070,460; 4,046,880; 4,038,144; 4,009,270; 3,975,519; 3,965,261; 3,853,993 and 3,788,468, largely by the inventor herein, directed to treating conditions including atherosclerosis, treatment of papillomas, treatment of spinal cord injuries, treatment of hypertension, and treatment of cerebral edema.

Notwithstanding these discoveries, certain obstacles remain to the large scale implantation of crocetin as a pharmaceutical for enhancing blood diffusivity in mammals, including humans. One problem is the preparation of the active agent in sufficiently pure and large amounts. Another, more serious problem is the fact that crocetin is nearly insoluble in aqueous solutions, making preparation of a drug for intravenous administration particularly difficult. Finally, reaching and maintaining adequate levels of crocetin to improve oxygen diffusivity, over a length of time, proves difficult.

Thus, is a goal of those of ordinary skill in the art to find a pharmaceutically acceptable drug which can be used to increase, over a sustained period, improvements in oxygen diffusivity, and thus oxygen uptake by the body tissues, in mammals.

SUMMARY OF THE INVENTION

The above objects, and others made more clear by the discussions set forth below, are achieved by the use of trans-sodium crocetinate, a crocetin salt obtained by treatment of crocetin, a diacid, with sodium hydroxide. It is important to note that only the trans-isomer is fully effective in meeting this goal. There are several isomeric forms of sodium crocetinate, but only the trans-isomer improves oxygen diffusivity. In fact, it appears that the other dominant form, the cis form, not only does not improve oxygen diffusivity, but negates the improvements obtained using the trans isomer.

The manufacture of sodium crocetinate by reacting crocetin with sodium hydroxide naturally forms both the cis and trans-isomers. The trans form may be isolated from this isomeric mixture by dissolving the mixture in methanol, precipitating TSC with a weak acid, and drying the precipitated material. It is important to note that the alcohol selected as a solvent appears to be important, methanol encouraging selection of the trans form.

TSC is demonstrated to be highly soluble in slightly alkaline aqueous solutions (pH 6.5–8.5) and is thus easily administered as a drug.

DETAILED DESCRIPTION OF THE INVENTION

Figure 1:
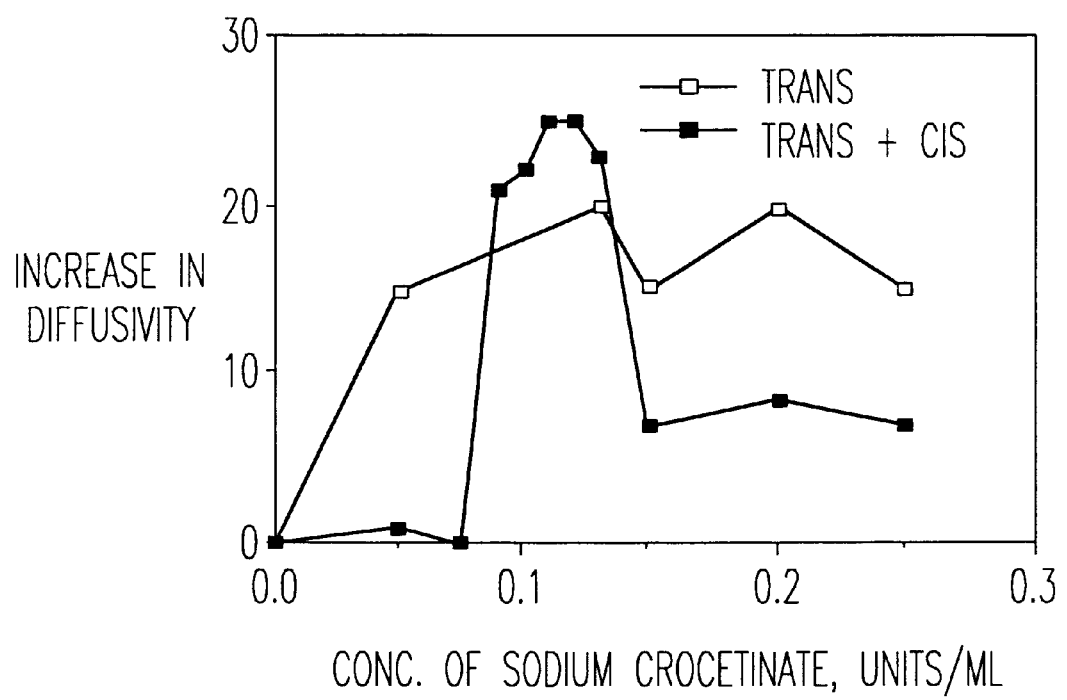
FIG. 1 is a graphic demonstration of the increase in diffusivity obtained, over time, by administration of the trans-isomer form of sodium crocetinate, and the trans and cis mixture.

TSC is formed by the reaction of crocetin, a diacid, with sodium hydroxide. This results in at least two isomeric forms, cis and trans, of sodium crocetinate. For reasons that remain uncertain, only the trans isomer is effective in increasing oxygen diffusivity. The cis form not only does not appear to be responsible for the increase in oxygen diffusivity through plasma, but appears to negate the effect after a certain level is achieved.

This isomeric selection phenomenon can be more clearly observed by reference to FIG. 1. A mixture of the trans and cis forms of sodium crocetinate causes an increase in the diffusivity of oxygen, but that effect disappears as their concentrations are increased. Studies demonstrate that the cis form negates the effect obtained, once a certain level is passed. In contrast, the increase in oxygen diffusivity is sustained when the concentration of only TSC is increased, as also shown in FIG. 1. This is of paramount importance in the therapeutic applications discussed below. The concentration of sodium crocetinate will continuously decrease once it is in the blood stream, clearance being effected through the blood stream associated clearance mechanisms. Thus, if the cis-trans mixture is given at a level where it is most effective, as shown in FIG. 1, it will soon be cleared from that level by the blood, and must be administered again. In contrast, TSC may be given at a higher concentration, with the result that the improvement in oxygen diffusivity is sustained over a longer period.

Sodium crocetinate is obtained by reacting crocetin with an adequate volume of sodium hydroxide. Any source of crocetin may be employed. Crocetin is a naturally-occurring carotenoid, and is otherwise available to those of skill in the art. It may be obtained from a large variety of natural sources, including saffron. To make TSC, saffron is extracted in a large volume of distilled, warm water, repeatedly, until the liquid in which the saffron is placed is no longer colored. All the colored liquid (a brown orange color) is combined.

This liquid is filtered, and the filtrate retained. To the filtrate is added sodium hydroxide, until the resulting solution has a pH of about 12–13. The solution is maintained at pH 12–13 for a period of about 2–12 hours, preferably 3–6.

Hydrochloric acid is added drop wise to the solution, while stirring, which induces precipitation at a pH of about 5–6. The solution changes to a cloudy orange color, the orange being due to the formation of the precipitate. Preferably, the solution is allowed to remain undisturbed, at temperatures between about 4–15° C., for a period of about 1–10 hours. The solution is centrifuged, and the liquid discarded. The remaining precipitate is washed with a slightly acidic solution, the base of which may be distilled water. Acids, such as citric acid may be used. The solution is then neutralized with sodium hydroxide until the pH is between 7–8, preferably, above 7.1. The neutralized solution is stored overnight (4–12 hours) in a non-reactive vessel, such as teflon coated vessel, at temperatures between about 0 and −10° C. A mixture of isomeric forms, including the trans and cis form, of sodium crocetinate is prepared.

TSC can be isolated by dissolving the mixture of isomers in methanol for a period of 30 minutes–12 hours. The trans isomer is precipitated from solution with a weak acid such as 0.5 N glacial acetic acid. A small amount of sodium hydroxide is added, preferably about 0.7 N, to the precipitate, to form the sodium salt. The material is dried, preferably through freeze drying. The result is pure TSC. It is important to note that the selection of the alcohol may be important. Although again, the reason is not clearly elucidated, it appears that methanol gives maximum recovery of TSC. TSC may be suspended, or dissolved in any pharmaceutically acceptable carrier for intravenous administration. Since the compound is directly soluble in blood plasma, it can be used either as a suspension, or dissolved in a buffered carrier having a slightly alkaline pH.

TSC can be used in the same pharmaceutical applications that have been established for crocetin, in the same effective amounts. Thus, the disclosures of the above-mentioned U.S. patents, specifically: U.S. Pat. Nos. 4,176,179; 4,070,460; 4,046,880; 4,038,144; 4,009,270; 3,975,519; 3,965,261; 3,853,933 and 3,788,468 are incorporated herein by reference. Methods have administration, including dosage regimes, are disclosed therein, and can be relied, substituting TSC for crocetin, noting that the solubility of TSC is greater.

Accordingly, TSC can be used anywhere, in mammals, where an improvement in oxygen diffusivity is desired. Among these conditions, hemorrhagic shock, a major source of battle field deaths, is effectively treated by administration of TSC, to improve oxygen diffusivity, and increase oxygen consumption. In hemorrhagic shock, normal oxygen consumption decreases to reduce blood flow rates, owing to ongoing hemorrhage. The decrease in oxygen consumption correlates with mortality. Wilson, Ann. Surg. 19:801–804 (1972). The effectiveness of improving survival rates by improving oxygen diffusivity through the use of crocetin, and thus, TSC, has been demonstrated by the inventor, Gainer, Circulatory Shock 41:1–7 (1993).

Another condition which can be treated and ameliorated by administration of TSC in place of crocetin is atherosclerosis. This is discussed in, e.g., U.S. Pat. No. 3,788,468. In particular, evidence suggests that atherosclerosis or hardening of the arteries, is initiated by reduction in the amount of oxygen reaching the blood vessel walls over a period of time. It is also known that the amount of oxygen used by the vascular wall decreases with age, which may correlate with the appearance of atherosclerosis in humans as they get older. Since much of the oxygen which reaches the inner third of the aorta comes directly from the blood flowing through these vessels, increasing the oxygen diffusion rate with crocetin was demonstrated to offset decreases in vascular oxygen levels.

This was demonstrated in the rabbit model, selected because it forms lesions or plaques on its main aorta artery after being fed a diet enhanced with 1% cholesterol. A study was conducted to determine if crocetin would result in reduction in the amount of plaque formed in rabbits fed such a cholesterol-enriched diet. Administration of crocetin caused a large decrease in the observed amount of legion covering three different sections of aorta, as compared with controls, who received an equal amount of saline solution in place of crocetin.

Administration of TSC, in place of crocetin, may be relied on to give equal results, and treating or ameliorating atherosclerosis conditions, noting that less TSC need be administered than crocetin, to obtain an equal effect.

Hypertension can similarly be addressed by the administration of TSC. U.S. Pat. No. 4,046,880 demonstrates methods of treating of hypertension with crocetin. In this case, the mammalian model is the rat. Rats were selected which develop hypertension spontaneously. Administration of crocetin was demonstrated to be effective in lowering blood pressure. Upon cessation of this administration, blood pressure again rose to levels exhibits by the control subjects. TSC administration, rather than crocetin, can be used to effectively control hypertension.

The leading cause of death in Western countries is ischemic heart disease. Death results from either a gradual deterioration of the ability of the heart to contract, or in many cases, a sudden stoppage. Myocardial ischemia exists when there is an insufficient supply of oxygen to the cardiac muscle. In this situation, the cardiac muscle cannot function, and dies. The area of the muscle is said to be "infarcted". Ischemia results in impairing mechanical and electrical performance and muscle cell injury, which may lead to a arrhythmia, ventricular fibrillation which, if untreated, is lethal.

Again using rats as the mammalian model (male Sprague-Dowley rats), the administration of crocetin was demonstrated to reduce both the incidence and duration of ventricular fibrillation. In additional experiments, areas of the heart which were infarcted due to deliberate occlusion of the vessel (either permanent or temporary) were considered. With a permanent occlusion, the size of infarction was the same whether or not the subject received crocetin, which would be expected, since the heart received no blood flow, and could not benefit from the increased oxygen diffusivity due to crocetin in the blood. With temporary occlusion, followed by reperfusion, administration of crocetin resulted in a decrease in both the infarcted and ischemic areas of the heart as well as an increase in the amount of normal tissue. Administration of TSC, in place of crocetin, enjoying superior solubility, and overall elevated level of effect, can be equally employed to treat ischemic heart disease. Another condition which is characterized by a decrease in oxygen consumption is emphysema, where the decrease in oxygen consumption is due to a increase in oxygen concentration in the blood, owing to damage to the alveolar sacks, resulting in less surface area available for oxygen/blood transfer. (In fact, the many small air sacks present in the lung collapse into larger one).

In a controlled study employing rats whose lung tissue was artificially damaged by the use of aerosolized enzymes, a dramatic increase in blood oxygen levels was achieved by administration of crocetin. Since blood volume delivery remains the same, total "oxygen delivery" can be achieved, notwithstanding the loss in blood oxygen concentration.

The effective dosage of TSC will depend upon the condition treated, the severity of the condition, the stage and individual characteristics of each mammalian patient addressed. Dosage ranges will vary, however, from about 0.001 mg active ingredient per kg of body per week up to about 150 mg, and preferably, from about 0.001–25 mg/kg of body weight per week. I.V. administration is preferred. Oral administration can be effected, however, the rate of transfer to the blood stream is reduced. In general, if oral administration is employed, greater dosages must be used.

Similarly, other conditions for which crocetin has been demonstrated as a useful treatment may be addressed by administration of TSC. These would include cerebral edema, papillomas spinal cord injuries and in general, disease states or conditions characterized by a drop in oxygen consumption in the body tissues.

This invention has been disclosed in terms of specific embodiments, and generic description. The specific embodiments are not intended as limiting, and variations will occur to those of ordinary skill in the art without the exercise of inventive skill. Such variations remain within the scope of the invention, save as excluded by the recitations of the claims set forth below. In particular, variations in dosage level, isolation procedure and specific condition will occur to those of ordinary skill in the art, without departing from the scope and spirit of the invention.

What is claimed is:

1. A method of increasing the oxygen diffusivity of oxygen in the blood stream of a mammal, comprising administering to said mammal a pharmaceutically effective amount of substantially pure TSC.

2. A pharmaceutical composition suitable for administration to a mammal, comprising substantially pure trans-sodium crocetinate (TSC) as the active ingredient.

3. The composition of claim 2, wherein said TSC is present with a pharmaceutically acceptable carrier.

4. The composition of claim 3, wherein said carrier is a buffered solution having a pH greater than 6.0.

5. Substantially pure trans-sodium crocetinate (TSC).

6. A method for recovering TSC from a mixture of isomeric forms of sodium crocetinate, comprising dissolving said isomeric mixture of sodium crocetinate in methanol, for a period of at least 30 minutes and adding to the resulting soltuion a weak acid so as to precipitate TSC.

* * * * *

UNITED STATES PATENT AND TRADEMARK OFFICE
CERTIFICATE OF CORRECTION

PATENT NO. : 6,060,511

DATED : May 9, 2000

INVENTOR(S): John L. GAINER

It is certified that an error appears in the above-identified patent and that said Letters Patent is hereby corrected as shown below:

In the Title Page,
Abstract [57], line 8, "crocetin, treat" should read --crocetin to treat--.

Column 1, line 40, " are controlled or be mediated" should read
--are controlled or mediated--.

Column 2, line 19, " Thus, is a goal" should read --Thus, it is a goal--.

Column 3, line 44, "such as teflon" should read --such as a teflon--.

Column 4, line 2, " Methods have administration" should read --Methods of administration--.

Column 4, line 3, " and can be relied" should read --and can be applied--.

Column 4, lines 10 and 11, " consumption decreases to reduce blood" should read --consumption decreases due to reduced blood--.

UNITED STATES PATENT AND TRADEMARK OFFICE
CERTIFICATE OF CORRECTION

PATENT NO. : 6,060,511  
Page 2 of 2

DATED : May 9, 2000

INVENTOR(S): John L. GAINER

It is certified that an error appears in the above-identified patent and that said Letters Patent is hereby corrected as shown below:

Column 4, line 39, " amount of legion" should read --amount of lesion--.

Column 4, line 54, " levels exhibits" should read --levels exhibited--.

Column 6, line 6, " papillomas spinal cord" should read --papillomas, spinal cord--.

Column 6, line 36, " soltuion" should read --solution--.

Signed and Sealed this

Seventeenth Day of April, 2001

*Attest:*

NICHOLAS P. GODICI

*Attesting Officer*     Acting Director of the United States Patent and Trademark Office

UNITED STATES PATENT AND TRADEMARK OFFICE
CERTIFICATE OF CORRECTION

PATENT NO. : 6,060,511  Page 1 of 1
DATED : May 9, 2000
INVENTOR(S) : Gainer, John L.

It is certified that error appears in the above-identified patent and that said Letters Patent is hereby corrected as shown below:

<u>Column 1,</u>
Line 10, the following paragraph should be inserted:

-- This application was made with Government support under Grant No. N00014-95-1-0213 by the Department of the Navy. The government has certain rights in the invention. --

Signed and Sealed this

Twenty-first Day of October, 2003

JAMES E. ROGAN
*Director of the United States Patent and Trademark Office*